(12) United States Patent
Chevalet et al.

(10) Patent No.: US 6,271,013 B1
(45) Date of Patent: Aug. 7, 2001

(54) *ASPERGILLUS NIGER* AMINOPEPTIDASE COMPOSITIONS FOR MAKING BREAD DOUGHS AND CHEESE

(75) Inventors: Laurent Chevalet, Annemasse; Jerome Souppe, Wasquehal; Joel De Leseleuc, Ognies; Jacky Brunet, Chateaugiron, all of (FR); Martinus J. M. Warmerdam, Rijswijk (NL)

(73) Assignee: DSM Patents and Trademarks, MA Delft (NL)

( * ) Notice: Subject to any disclaimer, the term of this patent is extended or adjusted under 35 U.S.C. 154(b) by 0 days.

(21) Appl. No.: 09/337,531

(22) Filed: Jun. 22, 1999

Related U.S. Application Data

(63) Continuation of application No. 08/776,484, filed as application No. PCT/EP96/02278 on Feb. 29, 1996, now Pat. No. 5,914,259.

(30) Foreign Application Priority Data

May 31, 1995 (EP) .................................. 95201425
Feb. 29, 1996 (EP) .................................. 96200533

(51) Int. Cl.$^7$ .............................. C12N 9/62; C12N 9/64; A23L 1/31
(52) U.S. Cl. ........................... 435/225; 435/226; 426/56
(58) Field of Search .................................. 435/431, 225, 435/404, 226, 420, 243; 426/56

(56) References Cited

U.S. PATENT DOCUMENTS

| 3,975,544 | 8/1976 | Kosikowski | 426/35 |
|---|---|---|---|
| 4,708,876 | 11/1987 | Yokoyama | 426/33 |
| 5,821,104 | * 10/1998 | Holm et al. | 435/225 |

FOREIGN PATENT DOCUMENTS

| 0 223 560 | 5/1987 | (EP) . |
|---|---|---|
| 0 384 303 | 8/1990 | (EP) . |
| 0 415 470 | 3/1991 | (EP) . |
| 75 160 472 | 12/1975 | (JP) . |
| 7 663 987 | 6/1976 | (JP) . |
| 03 143 394 | 6/1991 | (JP) . |
| 9 206 398 | 8/1992 | (KR) . |

OTHER PUBLICATIONS

Bosmann, H.B. *Biochim Biophys, Acta* (1973) 293:476–489.
Castaneda, R. et al. *Neth Milk Dairy J* (1990) 44(2):49–64.
Dal Degan, F. et al. *Appl Environm Microb* (1992) 56:2144–2152.
Hayashi, K. et al. *J Jpn Soc Food Sci Technol* (1990) 37(9):737–739.
Koaze, Y. et al. *Agr Biol Chem* (1964) 28(4):216–223.
Kumagai, I. et al. *Biochim Biophys, Acta* (1981) 659:334–343.
Kumagai, I. et al. *Biochim Biophys, Acta* (1981) 659:344–350.
Labbé, J. et al. "Action de leucine aminopeptidase I et II extracellulaire d'*Aspergillus oryzae*", *Experientia* 31(8):886–887 (Aug. 15, 1976).
Nakadai, T. et al. "Leucine aminopeptidase II," *Chemical Abstracts* 85(17):484; No. 121827 (Oct. 25, 1976).
Stevens, L. et al. *Revue roumaine de Biochimie* (1981) 18(1):63–66.
Stevens, L. *Biochem Soc Trans* (1985) 13(2):283–285.
Turkova, J. et al. *J. Biochim Biophys Acta* (1976) 420(2):309–315.
Lyublinskaya et al., Biospecific Sorbents for Purification of Aminopeptidases; e.g. *Aspergillus Niger* and *Bacillus Thuringiensis*, Bioorg.Khim., 10(2), 188–194, in BioTechds, AN 1984–05368, 1984.*
Coenen et al., "Safety Evaluation of Amino Peptidase Enzyme Preparation Derived from *Aspergillus Niger* ", Food and Chemical Toxicology, 36 (9–10) 781–789, Sep. 1998.*

* cited by examiner

*Primary Examiner*—Jon P. Weber
(74) *Attorney, Agent, or Firm*—Morrison & Foerster LLP

(57) ABSTRACT

Aminopeptidases originating from *Aspergilli niger* are disclosed, which can be produced in a fermentation broth or a liquid concentrate thereof substantially free of endoprotease. Such aminopeptidases may be advantageously employed in the food industry, e.g. in the preparation of bread doughs or cheese.

19 Claims, 3 Drawing Sheets

ASPERGILLUS NIGER AMINOPEPTIDASE COMPOSITIONS FOR MAKING BREAD DOUGHS AND CHEESE

This application is a continuation of Ser. No. 08/776,484, filed Jan. 30, 1997, now U.S. Pat. No. 5,914,259, which is a national stage of PCT/EP96/02278, International Filing Date, May 24, 1996, which claims benefit of EP 96200533.6, filed Feb. 29, 1996 and EP 95201425.6, filed May 31, 1995.

The present invention relates to aminopeptidases, their production and their industrial use.

Hydrolysis of proteins is of great importance, particularly in the food industry. It generally consists in transforming high molecular weight proteins (e.g. casein, gluten, gelatin, soy protein) into small fragments (oligopeptides or amino acids). These transformations may be carried out under highly acidic or highly alkaline conditions, which can often be energy consuming and requires the use of aggressive chemicals.

Protein degrading enzymes are preferred because they are less polluting and capable of working under mild conditions which prevents racemization of amino acids. These enzymes are classified into endoproteases and exopeptidases. Endoproteases cleave high molecular weight proteins into oligopeptides, whereas exopeptidases release amino acids from high molecular weight proteins or protein fragments.

Both types of enzyme are generally necessary to produce protein hydrolysates. The endo/exo ratio has to be varied according to the application. To obtain a strong liquefaction of a complex protein endo enzymes are required to provide the major hydrolysis contribution. Conversely, to produce specific amino acids or peptides from a complex protein without destroying its physical properties (elasticity, foaming property, texture property) exo enzymes with low endo activity will be preferred.

Many microorganisms are able to produce a endoprotease and exopeptidases. The endo/exo ratio is mainly dependent on culture conditions (1–3) and on downstream processing (4).

In the food industry, Aspergilli have been widely used for a long time and are therefore easily in conformity with regulations in many countries all over the world. Among Aspergilli, *Aspergillus niger* is the most widely used species in the food industry. Whereas endoprotease (5–7) are carboxypeptidase (5–10) from *Aspergillus niger* have been described, the production of aminopeptidases from *Aspergillus niger* has up to now not been known.

The present invention discloses aminopeptidases from selected *Aspergillus niger* strains and a method for producing them from appropriate cultures of *Aspergillus niger*. These aminopeptidases have an optimal activity at a pH in the range 6–8 and at a temperature in the range 50–60° C. Moreover, under appropriate culture conditions, aminopeptidases can be produced by selected *Aspergillus niger* strains substantially free of endoprotease. By "substantially free of endoprotease" is meant without detectable, or at least without a substantial amount of endoprotease. Thus, surprisingly, it has been found that by culturing selected *Aspergillus niger* strains a fermentation broth filtrate or liquid concentrate thereof can be obtained containing small amounts of endoprotease, but containing a high amount of aminopeptidase activity. Thus, a cell-free preparation of *Aspergillus niger* aminopeptidase may, for example, advantageously have at least 10 times more aminopeptidase activity, preferably at least 30 times more aminopeptidase activity, than endoprotease activity.

In view of recent changes in the nomenclature of black Aspergilli, the term *Aspergillus niger* is herein defined as including all (black) Aspergilli that can be found in the *Aspergillus niger* Group as defined by Raper and Fennell (1965, In: The Genus Aspergillus, The Williams & Wilkins Company, Baltimore, pp 293–344). Similarly, also for the other Aspergillus species we will refer to the Aspergillus groups as defined by Raper and Fennell supra. thereby including all species and variants included in a particular group by these authors.

A phenylalanine-aminopeptidase (Phe-AP) and a leucine-aminopeptidase (Leu-AP) have been identified and characterised in such preparations, the phenylalanine-aminopeptidase making the major contribution to the total aminopeptidase activity. It will be appreciated, however, that the invention also extends to preparations of functional derivatives of *Aspergillus niger* aminopeptidases substantially free of endoprotease.

Thus, in one aspect, the present invention provides a cell-free preparation of *Aspergillus niger* aminopeptidase or a functional derivative thereof which is substantially free of endoprotease.

In a further aspect, the present invention provides a process for preparing such an enzyme preparation which comprises fermenting an *Aspergillus niger* strain capable of producing aminopeptidase, e.g. *Aspergillus niger* NRRL 3112 or *Aspergillus niger* CBS 115.39, under conditions whereby aminopeptidase is produced in the fermentation broth, filtering the fermentation broth and optionally concentrating the filtrate thus obtained, e.g. by ultra-filtration (UF concentration). Preferably, concentration of the fermentation broth filtrate will be followed by addition of a stabilizing agent, preferably, for example, glycerol, e.g. at 50% (v/v). If desired, one or more aminopeptidases may be separated from the fermentation broth filtrate. The aminopeptidase is preferably substantially cell-free.

An aminopeptidase preparation according to the invention has several commercial applications. For example, such a preparation can be used advantageously for the preparation of baked products such as bread. 1 to 100 units Phe-AP, preferably 5 to 50 units Phe-AP per kg of dough results in an improved flavour and aroma for the baked product. Other uses can be found in food and feed applications such as cheese ripening, protein hydrolysates, debittering and yeast extract production.

Thus, in a still further aspect, the present invention provides a foot product or food preparation intermediate containing a preparation of *Aspergillus niger* aminopeptidase or a functional derivative thereof as hereinbefore described.

5 to 500 Phe-AP, preferably 15 to 250 Phe-AP per 1000 liters of milk results in an improved taste, flavour aroma, consistency and texture of the cheese at an earlier stage during ripening of the cheese.

We found that aminopeptidase is capable of producing free amino acids in semi hard cheese. An enzyme composition containing the aminopeptidase in conjunction with acid protease e.g. from *Mucor miehei* was found to be capable of producing bitterness reduced cheese.

In the cheesemaking process aminopeptidase is initially liberating rapidly high quantities of cheese flavour generating free amino acids. Surprisingly we found that the initial liberation of the free amino acids (see Example 5) stopped and did not result in overripening of cheese. This is in contrast with a lot of prior art processes wherein by the action of proteolytic enzymes this liberation of amino acids continues and which might result in overripening. A possible explanation of this continued liberation might be the combined action of endo and exoproteases.

The coagulants used in cheese making generally perform a vital role in proteolysis during the ripening of the cheese apart from the clotting activity they perform.

Traditionally all coagulants used in cheese making are enzyme preparations with one main enzymatic activity (protease) accompanied by some secondary enzymatic activities (in general also proteases), like for instance animal rennet in which chymosin and pepsin are predominantly responsible for both the coagulating action as well as for part of the proteolysis in cheese.

The same is true for microbial rennet from *Mucor miehei* and/or *Endothia parasitica*; in fact it is expected that the association of bitterness in cheese made of this type of coagulants could depend on its secondary enzyme activities.

When making cheese, scientific experiments do often not take into account variations in quality of incoming cheese milk at commercial cheese production plants. The incoming milk can easily be contaminated with exogenous enzyme systems deriving from the cow or from contaminating microorganisms. These contaminants are frequently insufficiently inactivated by the pasteurisation treatments used for cheese milk.

Attempts to accelerate cheese ripening at commercial scale, for instance by simply raising the ripening temperature, often encounter the drawback that good quality flavour is enhanced for cheeses derived from impeccable lots of milk but that defective milk lots just as often result in enhancing of off-flavours yielding a negative net gain.

The impact of above mentioned contaminants on cheese making parameters is thought to be one for this assessment.

The secondary activities of coagulant enzymes are also to be held partially responsible for the amplification of the off-flavours produced in those occasions.

The use of conventional and existing blends of accelerated ripening enzymes, invariably mixtures of crude endo- and exopeptidases, provide a similar and additional risk; probably even the greatest of the three.

Therefore the aminopeptidase with standardised activity and free of endopeptidase activity is preferably used in combination with a standardised preparation of fermentation derived chymosin, with standardised and known endopeptidase activity and free from pepsin and/or other contaminating proteases.

Preferably also neutral protease is added more preferably neutral protease from Bacillus, more preferably from *Bacillus subtilis*, with standardised endopeptidase activity free from secondary and serine protease activities. Possible routes to obtain purified neutral protease are a concentration and purification process starting with a fermentation broth containing the neutral protease. Another possibility is the production in a transformed host, which system is designed for its selective production of the desired enzyme.

These enzyme compositions allow for the development of a cheese making process in which the acceleration of cheese maturation takes place under reduced risk of producing off flavours as associated with occasional fluctuations in milk quality and incidental variations in the cheese making process.

An enzyme composition consisting of at least the aminopeptidase and a neutral protease, was found to be capable of producing good quality hard gratable cheese, swiss flavour type.

This enzyme composition is capable of texturing the curd of hard cooked cheese types in such a way that texture characteristics of the cheese become positively modified.

Moreover, this enzyme composition allows for the development of a modified production process of hard gratable swiss flavour type of cheese with a reduced ripening time.

This enzyme composition, under addition of an a-specific coagulant, allows for the development of a production process for the production of hard, cooked curd cheeses hereby increasing moisture content without compromising on texture at the same time.

The starter cultures used for the production fermented products like yoghurt, cheese and sausages dispose of several intra- and extracellular enzyme systems of, amongst others, proteolytic and lipolytic nature.

The purpose of these enzyme systems are at least twofold:
a) for reproduction and growth
b) for fermenting and maturing the food stuff To a certain extent the two functions coincide: carbohydrate uptake and degradation serves to grow but as by products lactic acid is being produced. This lactic acid is predominantly responsible for the acidification and preservation of the fermented food stuff.

For uptake of amino acids and lipids, both building blocks for growth, the bacteria use their extra cellular enzymes to liberate these building blocks from the media they are inoculated upon; i.e. milk or meat in the example. The proteolysis and lipolysis thus taking place in the food stuff are major contributors in the ripening and maturation of the food products like cheese and sausages.

Traditional insight in proteolysis and lipolysis by starter cultures refer to a need for a balanced set of extracellular, cell envelope, membrane-linked and intracelular enzymes. Following these theories the well balanced ratio of these enzyme systems are to be held responsible for the production of sufficient amounts of SN (soluble nitrogen) and AN (amino acid nitrogen). Basically, endopeptidasic activities of rennet, starter and exogenous enzymes result in a rapid degradation of paracasein in cheese curds into smaller peptides.

These smaller peptides are subsequently transformed into amino acids by active starter cells. Flavour and aroma compounds are then produced via many complex enzymatic and chemical reactions.

It has been relatively well known that lysis of starter cells is a prerequisite for the production of free amino acids in cheese.

Recently it has been demonstrated that lysis is predominantly taking place in the very early stages of cheese ripening.

We have found that highly proteolytic starter bacteria, that are mainly chosen for their rapid acidification properties, do not easily lyse in the young cheese and therefore easily lead to enhance bitterness in older cheese due to their reduced ability to transform bitter peptides into amino acids and their high proteolytic activity in cheese.

In the preparation of an inoculum often nutrient-rich media are used for rapid bacteria propagation. These media are rich, amongst others, in carefully selected, blended and/or pretreated proteins, yeast extracts, vitamins and minerals.

We have now found that an improved culture medium and a process for the production thereof can be obtained under the utilisation of yeast extracts treated with the present aminopeptidase. Instead of yeast extracts also other protein sources of proteinatious material can be used (e.g. whey). Under application of this newly developed culture medium, also an improved starter culture can be obtained.

This implies development of a rapid acidifying fermented milk and cheese culture by using media containing aminopeptidase treated proteins and yeast extracts, avoiding the accompanying defect of producing, for instance, bitterness in cheese.

Advantages are an increased capacity of milk processing or a dosage reduction in cultures used, and reduced risks for bitterness.

The necessary free amino acids for rapid growth in the cheese milk are to be provided by the addition of aminopeptidase to the cheese milk or by traditional cultures, possibly to be used in combination with our specially developed culture.

Therefore the present invention provides an improved cheese culture for cheese manufacture and a process for production and propagation of the cheese culture under using the present aminopeptidase in the production in the culture medium.

A composition comprising aminopeptidase, chymosin, neutral protease in combination with the above mentioned starter cultures results in a standardised production of cheese. The advantage is that fluctuations in milk quality and cheese making conditions have less consequences in ripening of the cheese.

LEGENDS TO THE FIGURE

DETERMINATION OF ENZYMATIC ACTIVITIES

1 -Phenylalanine-aminopeptidase (Phe-AP)

Figure 1:
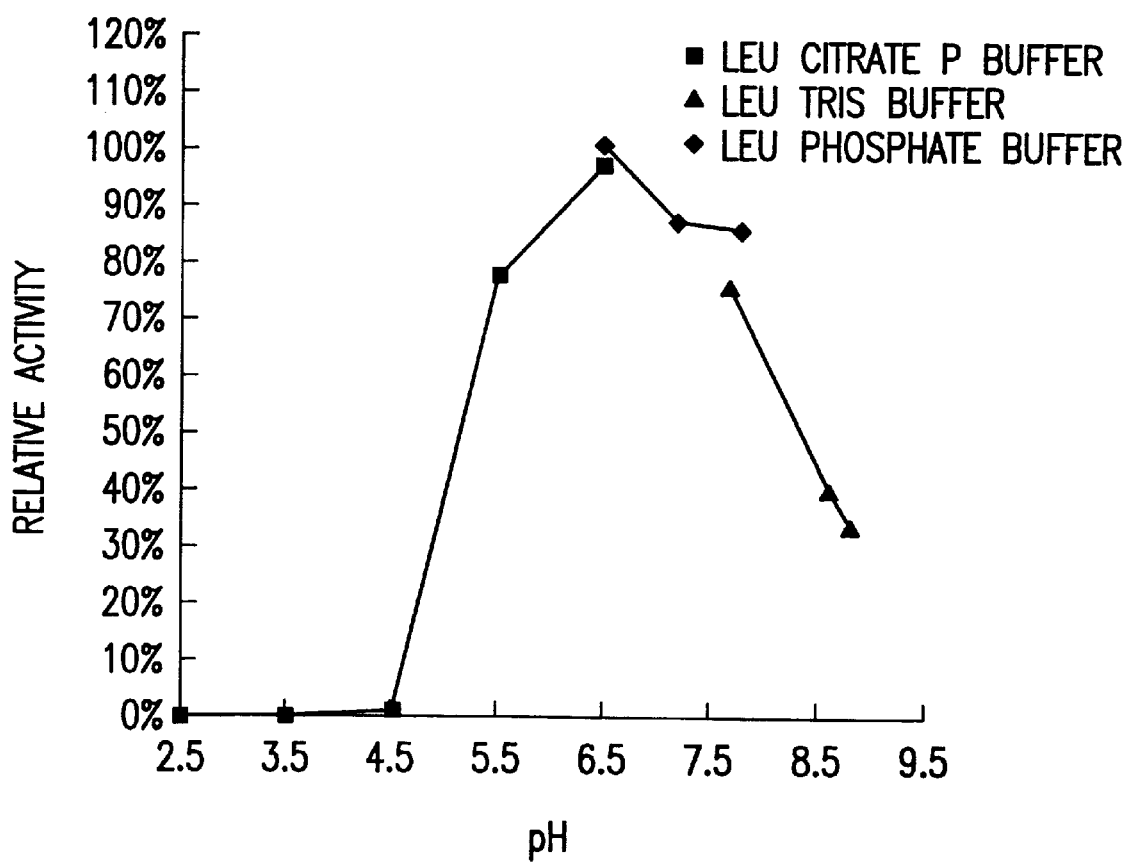
FIG. 1 shows the pH profile of leucine-aminopeptidase from *Aspergillus niger*.

Phenylalanine paranitroanilid was dissolved in 7.5 mM HCl at a concentration of 0.9 mM. 1 ml of that substrate solution was mixed with 1.5 ml 0.1M phosphate buffer pH 7.2. At t=0, 0.5 ml enzyme was introduced and left for reaction at 20° C. 1 ml HCl was added 15 minutes later. A blank was run with 1N HCl being introduced at t=0. Optical density was determined for the bland ($OD_{blank}$) and for the assay ($OD_{assay}$) at 400 nm. Activity was calculated as follows:

$$A = \frac{(OD_{assay} - OD_{blank})}{9.8 \times 15} \times \frac{4}{0.5} \text{ Phe-AP}/\text{ml}$$

2 -Leucine-aminopeptidase (Leu-AP)

Leucine paranitroanilid was dissolved in water at a concentration of 9 mM. 1 ml of that substrate solution was mixed with 1.5 ml 0.1M phosphate buffer pH 7.2. At t=0.5 ml enzyme was introduced and left for reaction at 20° C. 1 ml 1N was added 15 minutes later. A blank was run with 1N HCl being introduced at t=0. Optical density was determined for the blank ($OD_{blank}$) and for the assay ($OD_{assay}$) at 400 nm. Activity was calculated as follows:

$$A = \frac{(OD_{assay} - OD_{blank})}{9.8 \times 15} \times \frac{4}{0.5} \text{ Leu-AP}/\text{ml}$$

3 -Valine-aminopeptidase (Val-AP)

Valine paranitroanilid was dissolved in water at a concentration of 9 mM. 1 ml of that substrate solution was mixed with 1.5 ml 0.1M phosphate buffer pH 7.2. At t=0, 0.5 ml enzyme was introduced and left for reaction at 20° C. 1 ml HCl was added 15 minutes later. A blank was run with 1N HCl being introduced at t=0. Optical density was determined for the blank ($OD_{blank}$) and for the assay ($OD_{assay}$) at 400 nm. Activity was calculated as follows:

$$A = \frac{(OD_{assay} - OD_{blank})}{9.8 \times 15} \times \frac{4}{0.5} \text{ Val-AP}/\text{ml}$$

4 -Endoprotease (PU)

This activity is measured by the hydrolysis of casein at pH 6.0, 4° C. for 1 h. One PU is the amount of enzyme needed to liberate the equivalent of 1 μmole tyrosine per minute after precipitation of the remaining proteins with trichloracetic acid.

EXAMPLE 1

Screening of *Aspergillus niger* strains

200 *Aspergillus niger* strains, isolated from different sources or obtained from culture collections, were grown in a medium containing 15 g/l potato flour, 20 g/l bactopeptone, 7 g/l yeast extract, 4 g/l potassium dihydrogenphosphate, 0.5 g/l magnesium sulfate, 0.5 g/l calcium chloride, 0.5 g/l zinc chloride. pH was 4.8. After 24 h. preculture at 240 rpm 30° C. and 96 h culture at 275 rpm 30° C., supernatants were collected and assayed for leucine- phenylalanine- and valine-aminopeptidase activity as described above. Several *Aspergillus niger* strains showed high production potentials for at least one of these enzymatic activities, as shown in Table 1 (each value is a mean value from four individual results):

TABLE 1

| Strain number | aminopeptidase activities in supernatants | | | endopeptidase |
|---|---|---|---|---|
| | Leu-AP/1 | Phe-AP/1 | Val-AP/1 | PU/ml |
| 1053 | 25 | 170 | 32 | <0.1 |
| 1085 | 23 | 135 | 48 | 0.1 |
| 1103 | 37 | 285 | 40 | 0.1 |
| 1108 | 60 | 435 | 29 | 0.1 |
| 1444 | 40 | 192 | 50 | 0.1 |
| 1497 | 25 | 105 | 75 | 0.1 |
| 1502 | 16 | 44 | 63 | 0.1 |

Amongst the above strains, strains 1108 and 1502 were obtained from a culture collection and were deposited under the accession numbers NRRL 3112 and CBS 115.39, respectively. Strain NRRL 3112 has been used for the production of aminopeptidase, α-amylase and glucoamylase. Strains CBS 115.39 has been used for the production of amylase or lipase.

EXAMPLE 2

Production of exopeptidase at laboratory scale

Some strains from the screening described in Example 1 have been fermented in laboratory fermentors (10 liters). Results obtained with strain 1502 are presented in this Example.

Spores of *Aspergillus niger* strain No. 1502 were collected on PDA-plates after 7–10 days of incubation at 30° C. An inoculum step was performed in a shake flask in a medium composed of glucose (20 g/l) and corn steep (20 g/l) at pH 4.8 over 24 h.

The main fermentation was performed according to a batch process. The following nutrients were used: 100 g/l maltodextrins, 40 g/l soy bean flour, 40 g/l hydrolysed casein, 5 g/l corn steep, 2 g/l gelatin, 2 g/l potassium dihydrogenphosphate, 1.3 g/l sodium nitrate, 1 g/l ammonium chloride, 0.01 g/l iron sulfate and 0.5 g/l antifoaming agent.

All nutrients were firstly mixed together except the maltodextrins, pH was adjusted to 4.8±0.1. The fermentor was then sterilized at 125° C. for 40 minutes. The maltodextrin solution was sterilized separately and added to the sterile but cooled fermentation medium.

The main fermentation was run in a laboratory fermentor which was filled with 6 liters of the medium described above and inoculated with the inoculum flask. Stirring and air provision were adjusted to maintain the dissolved oxygen concentration as high as possible. The temperature was maintained at 30° C. The fermentation was stopped when all the nutrients had been consumed, i.e. after about 130 hours.

The fermentation broth was filtered to remove all microorganisms. Aminopeptidase and endoprotease activities were measured in the filtrate:

| | |
|---|---|
| 0.15 | Leu-AP/ml |
| 1.0 | Phe-AP/ml |
| <0.05 | Val-AP/ml |
| <0.1 | PU/ml |

UF concentration was then performed to formulate liquid aminopeptidase, glycerol (50%) being the stabilizing agent. The resulting solution called 'Peptidase L2' had the following activities:

| | |
|---|---|
| 0.5 | Leu-AP/ml |
| 3.2 | Phe-AP/ml |
| <0.05 | Val-AP/ml |
| <0.1 | PU/ml |

These results show that the selected *Aspergillus niger* strain grown under our selected conditions produces aminopeptidases without substantial amounts of endoprotease.

EXAMPLE 3 pH profiles of enzymatic activities

Leu-AP and Phe-AP activities were determined in Peptidase L2 (see Example 2) using different buffers to screen a pH range from 2.5 to 9.0.

The pH profile of leucine-aminopeptidase from *Aspergillus niger* is shown in FIG. 1.

Figure 2:
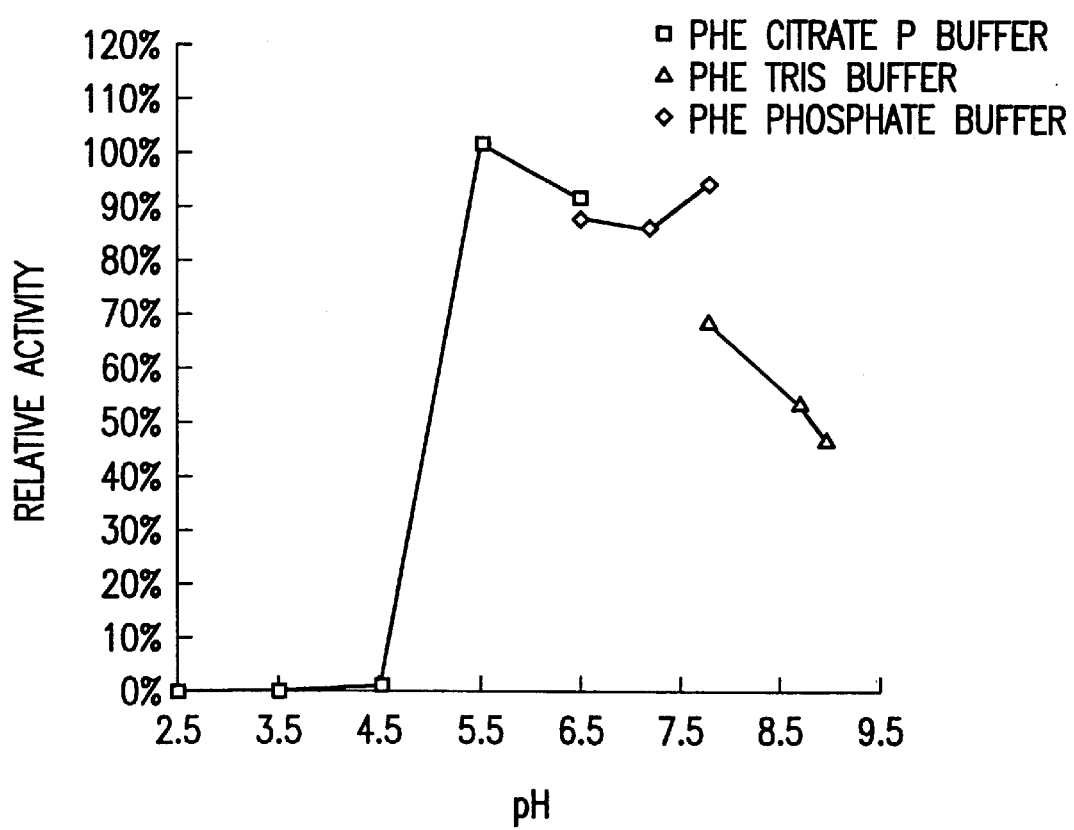
FIG. 2 shows the pH profile of phenylalanine-aminopeptidase from *Aspergillus niger*.

The pH profile of phenylalanine-aminopeptidase from *Aspergillus niger* is shown in FIG. 2.

The Figures show that Leu-AP is active in the pH range from 5 to 8.5, whereas Phe-AP is active in the pH range from 5.5 to 9 which is similar to aminopeptidases from other Aspergillus species.

EXAMPLE 4

Temperature profile of enzymatic activities

Leu-AP and Phe-AP activities were determined in Peptidase L2 (see Example 2) using different incubation temperatures to screen a temperature range from 5 to 70° C.

Figure 3:
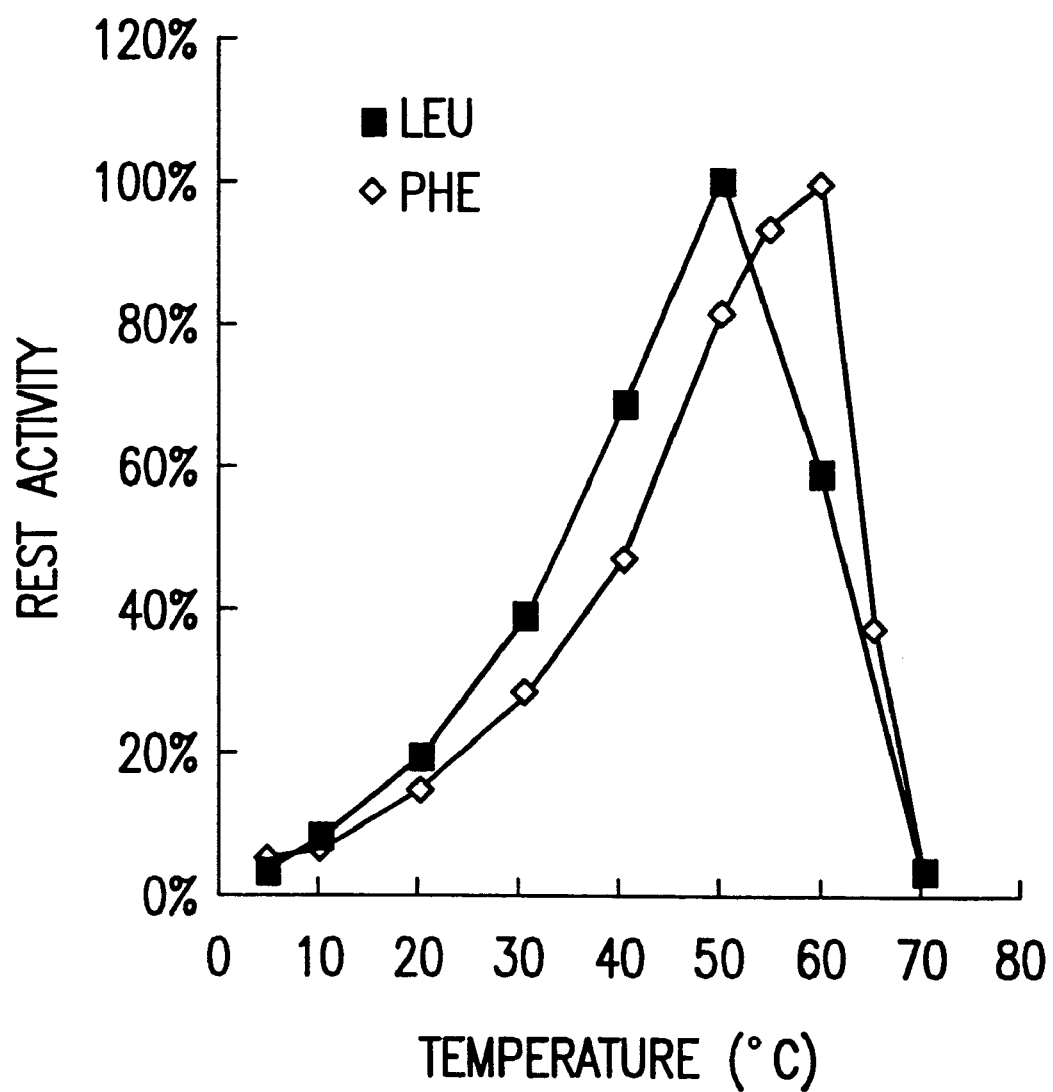
FIG. 3 shows the temperature profile of both aminopeptidases

The resulting temperature profiles are shown in FIG. 3. The results show that each enzyme has a different optimal temperature, i.e. 50° C. for Leu-AP and 60° C. for Phe-AP.

EXAMPLE 5

The production of semi hard cheese at laboratory scale.

Normal cheese milk was inoculated with starter cultures and renneting was executed with an average dosage of animal rennet (1:15.000 MCU; Control 1) To the first experimental batch of milk 25 Phe-AP units per thousand liters of milk added.

In a second trial, the animal rennet was substituted by microbial rennet: the acid protease from *Mucor miehei*. The experimental lot contained again 25 Phe-AP units of aminopeptidase was substituted with a commercial enzyme preparation derived from *A. oryzea*. This preparation consists of an endopeptidase/exopeptidase activity.

Cheese making parameters were maintained conform the procedure applied for semi hard cheese for all four cheese lots.

After the subsequent brining of the cheese the ripening was performed at 8° C.

Related to experiment 1, during the course of maturation, a difference was noted in terms of flavour and aroma development between experimental cheeses and control cheese to such an extent that the experimental cheese had obtained most of their required organoleptical properties after three (3) weeks whereas the control cheeses had obtained a similar qualification after six (6) weeks.

The level of free amino acids after three weeks of maturation was shown to be twice as high in the experimental cheese; after six weeks of ripening the levels were comparable again. This suggests that the product is ready for sale three weeks earlier without decreasing the keeping quality of the cheese. In this experiment we showed that the ripening can be accelerated by the initial increase of the liberation of amino acids whereas no overripening has been observed.

For experiment 2, the organoleptics of the cheese different to the extent that the bland cheese flavour with a slight tendency to bitterness of the control cheese was overcome in the experimental cheeses in the presence of aminopeptidase. The texture of the cheese was found to be somewhat smoother as well.

The results of experiment 3 showed both a higher level of free amino acids and at the same time a higher bitter score in the organoleptic evaluation, suggesting that the endopeptidase activity enhances bitterness/

EXAMPLE 6

The production of swiss type hard cheese at laboratory scale.

Normal cheese milk was inoculated with starter cultures and coagulant was added (acid protease from *Endothia parasitica*).

To the experimental lot of milk an enzyme mixture consisting of 9000 units endoprotease (from Neutral Protease B 500) and 15 Phe-AP units of aminopeptidase, calculated per 1000 liters of milk, were added.

Cheesemaking parameters were kept conform the recipe during the rest of the experiment.

After bringing the cheese were pre-incubated at 13° C. for 20 days to prepare the texture of curd and subsequently incubated at 19° C. for another 35 days in order to stimulate propionic acid fermentation.

The results surprisingly showed absence of bitterness, a well known defect of the utilisation of this neutral protease in cheesemaking, absence of holes (eyes) but with good and typical taste and flavour development, a good gratable cheese with excellent melting properties at a lower dry matter content of the cheese; 60.5% in the control versus 57.8 in the experimental cheese.

A repetition of this trial was performed in which the coagulant was substituted with Fromase® and in which the pre-incubation at 13° C. lasted 10 days and the incubation at 19° C. lasted 20 days. The total ripening time was halved.

The results of this trial were largely comparable with the first one.

REFERENCES (1) HAYASHI, K.; CLIFFE, A. S.; LAW, B. A. J. Jpn Soc. Food Sci. Technol. (1990), 37 (9) 737–739

(2) CASTANEDA R.; VASSAL L; GRIPON, J. C.; ROUSSEAU, M. Neth. Milk Dairy J. (1990) 44 (2) 49–64

(3) STEVENS, L. Biochem. Soc. Trans (1985) 13 (2) 283–285

(4) TURKOVA, J.; VALENTOVA, O.; COUPER, J. Biochim Biophys. Acta (1976) 420 (2) 309–315

(5) KOAZE, Y.; GOI, H.; EZAWA, K.; YAMADA, Y.; HARA, T. Agr. Biol. Chem. (1964) 28 (4) 216–223

(6) STEVENS, L.; HULEA, S. A.; DUNCAN, D.; VASU, S.; BRAD, I. Revue romaine de Biochimie (1981) 18 (1) 63–66

(7) BOSMANN, H. B. Biochim. Biophys. Acta (1973) 293, 476–489

(8) DAL DEGAN, F.; RIBADEAU-DUMAS, B.; BREDDAM, K. Appl. Environm. Microb. (1992) 58, 2144–2152

(9) KUMAGAI, I.; YAMASAKI, M. Biochim. Biophys, Acta (1981) 659, 344–350

(10) KUMAGAI I.; YAMASAKI, M. Biochim. Biophys, Acta (1981) 659, 334–343

What is claimed is:

1. A composition comprising an *Aspergillus niger* aminopeptidase preparation and an enzymatic cheese-making coagulant wherein said preparation has 10 times more units of aminopeptidase activity than units of endoprotease activity and the aminopeptidase activity is phenylalanine aminopeptidase and/or leucine aminopeptidase.

2. A process to prepare a starter culture which comprises culturing a selected microbial culture on a culture medium, containing at least a yeast extract or another proteineous material either of which has been previously treated with the composition of claim 1, to form sufficient amounts of soluble nitrogen and amino acid nitrogen, wherein the culturing continues for a time sufficient to form a balanced set of extracellular, cell envelope, membrane-linked and intracellular enzymes.

3. The composition of claim 1 wherein said coagulant is an acid protease.

4. The composition of claim 3 wherein said acid protease is of microbial origin.

5. The composition of claim 4 wherein said microbe is of the genus Mucor or Endothia.

6. The composition of claim 3 wherein said coagulant is an animal protease.

7. The composition of claim 3 wherein said coagulant is a vegetable protease.

8. A composition comprising an *Aspergillus niger* aminopeptidase preparation and a neutral protease, wherein said preparation has 10 times more units of aminopeptidase activity than units of endoprotease activity and the aminopeptidase activity is phenylalanine aminopeptidase and/or leucine aminopeptidase.

9. The composition of claim 8 wherein the neutral protease is from Bacillus.

10. Process for the production of cheese comprising contacting milk with a starter culture and the composition according to claim 1 or 8.

11. Process for the production of cheese according to claim 10 wherein the cheese is a Swiss type hard cheese.

12. A process for the production of cheese according to claim 10 wherein the *Aspergillus niger* aminopeptidase is at levels of 5 to 250 units per 1,000 liters of milk.

13. A method to prepare a food product which method comprises contacting a precursor of said product with the composition according to claim 1.

14. A method for preparation of a feed product which method comprises contacting a precursor of said product with the composition according to claim 1.

15. The composition of claim 1 wherein the *Aspergillus niger* aminopeptidase is contained in a fermentation broth filtrate or a liquid concentrate thereof, optionally containing glycerol as a stabilizing agent.

16. In a medium for production of a starter culture for the production of fermented food products wherein the improvement comprises an *Aspergillus niger* aminopeptidase, wherein the *Aspergillus niger* aminopeptidase has 10 times more activity of aminopeptidase than units of endoprotease and the aminopeptidase activity is phenylalanine aminopeptidase and/or leucine aminopeptidase.

17. In a food product or food preparation intermediate containing aminopeptidase wherein the improvement comprises a preparation of *Aspergillus niger* aminopeptidase wherein the *Aspergillus niger* aminopeptidase has 10 times more activity of aminopeptidase than units of endoprotease and the aminopeptidase activity is phenylalanine aminopeptidase and/or leucine aminopeptidase.

18. In a baked product dough wherein the improvement comprises *Aspergillus niger* aminopeptidase, wherein the aminopeptidase wherein the *Aspergillus niger* aminopeptidase has 10 times more activity of aminopeptidase than units of endoprotease and the aminopeptidase activity is phenylalanine aminopeptidase and/or leucine aminopeptidase.

19. The baked product dough of claim 18 wherein the *Aspergillus niger* aminopeptidase is present in amounts of 1 to 100 units per kg of dough.

* * * * *